US011633505B2

(12) United States Patent
Yoneda et al.

(10) Patent No.: US 11,633,505 B2
(45) Date of Patent: Apr. 25, 2023

(54) NUCLEAR MAGNETIC RESONANCE DIAGNOSTIC AGENT, AND METHOD FOR DETECTING OR DIAGNOSING STATE OF CELL, TISSUE OR ORGAN IN SUBJECT USING SAME

(71) Applicants: National University Corporation Kumamoto University, Kumamoto (JP); University Of Occupational And Environmental Health, Japan, Fukuoka (JP); SBI Pharmaceuticals Co., Ltd., Tokyo (JP)

(72) Inventors: Tetsuya Yoneda, Kumamoto (JP); Shigeru Nishizawa, Fukuoka (JP); Junkoh Yamamoto, Fukuoka (JP); Tohru Tanaka, Tokyo (JP); Hidenori Itoh, Tokyo (JP)

(73) Assignees: National University Corporation Kumamoto University, Kumamoto (JP); University of Occupational and Enviromental Health, Japan, Kitakyushu (JP); SBI Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 14/650,530

(22) PCT Filed: Dec. 9, 2013

(86) PCT No.: PCT/JP2013/082974
§ 371 (c)(1),
(2) Date: Jun. 8, 2015

(87) PCT Pub. No.: WO2014/092051
PCT Pub. Date: Jun. 19, 2014

(65) Prior Publication Data
US 2015/0320888 A1    Nov. 12, 2015

(30) Foreign Application Priority Data
Dec. 11, 2012    (JP) .............................. JP2012-270844

(51) Int. Cl.
| A61K 49/10 | (2006.01) |
| C07C 229/22 | (2006.01) |
| A61B 5/055 | (2006.01) |
| G01R 33/56 | (2006.01) |
| A61K 49/18 | (2006.01) |

(52) U.S. Cl.
CPC ............ A61K 49/103 (2013.01); A61B 5/055 (2013.01); A61K 49/10 (2013.01); A61K 49/1836 (2013.01); C07C 229/22 (2013.01); G01R 33/5601 (2013.01)

(58) Field of Classification Search
CPC ............................. A61K 49/103; C07C 229/22

USPC ......................................................... 424/9.3
See application file for complete search history.

(56) References Cited

U.S. PATENT DOCUMENTS

| 4,986,256 A   * | 1/1991  | Cohen et al. ............... 424/9.362 |
| 5,169,944 A     | 12/1992 | Nelson et al. |
| 2003/0065029 A1 * | 4/2003  | Tanaka et al. ................. 514/561 |
| 2006/0135868 A1 * | 6/2006  | Salomon et al. ............. 600/411 |
| 2011/0275932 A1 * | 11/2011 | Leblond ............... A61B 5/0062 600/425 |

FOREIGN PATENT DOCUMENTS

| EP | 995448 A1 | 4/2000 |
| EP | 2135613 A1 | 12/2009 |
| EP | 2272538 A1 | 1/2011 |
| JP | H11-12197 A | 1/1999 |
| JP | 2005524461 A | 8/2005 |
| JP | 2006124372 A | 5/2006 |
| JP | 2009298739 A | 12/2009 |
| JP | 2011026221 A | 2/2011 |
| WO | WO 1991001727 | 2/1991 |
| WO | 2003094695 A2 | 11/2003 |
| WO | 2006096492 A2 | 9/2006 |
| WO | 2008126693 A1 | 10/2008 |
| WO | 2009130893 A1 | 10/2009 |
| WO | 2009157561 A1 | 12/2009 |
| WO | 2014092051 A1 | 6/2014 |

OTHER PUBLICATIONS

Bartosova et al. Comp. Biochem. Phys. Part C 2000, 126, 245-252.*
Suto et al. Acta Radiological 1993, 34, 226-229.*
Braakham et al. J. Mag. Res. Imag. 2006, 24, 530-536. (Year: 2006).*
Carapella et al., "The Role of Flourescence-Guided Surgical Resection in the Combined Treatment of Malignant Glioma," J Clin Oncol, 30, 2012, 2 pgs.

(Continued)

*Primary Examiner* — Michael G. Hartley
*Assistant Examiner* — Sean R Donohue
(74) *Attorney, Agent, or Firm* — Cynthia Hathaway; Lauren L. Stevens

(57) ABSTRACT

[Problem]
To provide a nuclear magnetic resonance diagnostic agent that has a lower toxicity to organisms and reduced side effects and yet has a site specificity toward a specific cell, tissue, organ, etc.
[Solution]
When ALA or an ALA derivative is administered in vivo, a metabolite thereof is accumulated in a specific cell, tissue, organ, etc. Focusing on this phenomenon, a nuclear magnetic resonance analysis was performed on a site wherein the metabolite of ALA that had been administered in vivo would be possibly accumulated. As a result, it was surprisingly found that ALA and an ALA derivative are useful as a diagnostic agent whereby the aforesaid problem can be solved.

4 Claims, 3 Drawing Sheets

(56) References Cited

OTHER PUBLICATIONS

Roberts et al., "Coregistered Fluorescence-Enhanced Tumor Resection of Malignant Glioma: Relationships Between δ-aminolevulinic Acid-Induced Protoporphyrin IX Fluorescence, Magnetic Resonance Imaging Enhancement, and Neuropathological Parameters," J Neurosurg., 114(3):595-603, Mar. 2011, 9 pgs.

Tsugu et al., "Impact of the Combination 5-Aminolevulinic Acid-Induced Fluorescence with Intraoperative Magnetic Resonance Imaging-Guided Surgery for Glioma," World Neurosurgery, vol. 76, Issues 1-2, Jul.-Aug. 2011, 8 pgs.

Cho HR et al., Malignant glioma: MR imaging by using 5-aminolevulinic acid in an animal model, Radiology, Sep. 2014;272(3): pp. 720-730.

Ganzer R. et al., Intraoperative Photodynamic Evaluation of Surgical Margins During Endoscopic Extraperitoneal Radical Prostatectomy with the Use of 5-Aminolevulinic Acid, Journal of Endourology, Sep. 2009.

Ladner DP et al., Photodynamic diagnosis of breast tumours after oral application of aminolevulinic acid, British Journal of Cancer (2001).

Zaak D et al., Photodynamic Diagnosis of Prostate Cancer Using 5-Aminolevulinic Acid—First Clinical Experiences, Urology, (Apr. 11, 2008).

Aime, S. et al., "A New Class of Contrast Agents for Magnetic Resonance Imaging Based on Selective Reduction of Water-T2 by Chemical Exchange", Investigative Radiology, Philadelphia, PA, US, vol. 23, No. Suppl. 1, pp. S267-S270, (Jan. 1, 19988).

Ishizuka, M. et al., "Novel Development of 5-Aminolevurinic Acid (ALA) in Cancer Diagnoses and Therapy", Int Immunopharmacol., 11(3):358-65, (2011).

Kemmner, W. et al., "Silencing of Human Ferrochelatase Causes Abundant Protoporphyrin-IX Accumulation in Colon Cancer", FASEB J., 22(2):500-9, (2008).

Lin, F. et al., "Protoporphyrin IX-Sensitized Photoinactivation of 5-Aminolevulinate-Treated Leukemia Cells: Effects of Exogenous Iron", Photochem Photobiol., 69(3):375-81, (1999).

Miyake, M. et al., "siRNA-Mediated Knockdown of the Heme Synthesis and Degradation Pathways: Modulation of Treatment Effect of 5-Aminolevulinic Acid-Based Photodynamic Therapy in Urothelial Cancer Cell Lines", Photochem Photobiol., 85(4):1020-7, (2009).

Teng, L. et al., "Silencing of Ferrochelatase Enhances 5-Aminolevulinic Acid-based Fluorescence and Photodynamic Therapy Efficacy", Br J Cancer, 104(5):798-807, (2011).

Hogers, B. et al., "Magnetic Resonance Microscopy of Mouse Embryos in Utero", Anat Rec., 260(4):373-7, (2000).

\* cited by examiner

NUCLEAR MAGNETIC RESONANCE DIAGNOSTIC AGENT, AND METHOD FOR DETECTING OR DIAGNOSING STATE OF CELL, TISSUE OR ORGAN IN SUBJECT USING SAME

This application is a National Phase Entry under 35 U.S.C. § 371 of application No. PCT/JP2013/082974, filed Dec. 9, 2013, which claims the benefit under 35 U.S.C. § 119 of Japanese application No. 2012-270844, filed Dec. 11, 2012, the disclosures of which are incorporated by reference as if written herein in their entireties.

TECHNICAL FIELD

The present invention relates to a nuclear magnetic resonance diagnostic agent, and more specifically to a nuclear magnetic resonance diagnostic agent comprising 5-aminolevulinic acid or a derivative thereof, or a salt thereof. Moreover, the present invention also relates to a method for detecting or diagnosing a state of a cell, tissue or organ in a subject, using the aforementioned nuclear magnetic resonance diagnostic agent, or a method for obtaining a T2-weighted image in which the contrast is increased in MRI.

BACKGROUND ART

For in vivo diagnoses of diseases or conditions, for example, X-ray CT (computed tomography), PET (positron emission tomography), MRI (magnetic resonance imaging), and the like have been utilized.

However, X-ray CT has been problematic in terms of external exposure to X-ray irradiation upon examination.

In addition, PET requires administration of a radioisotope such as $^{11}$C-methionine as a tracer into a living body. Thus, PET has been problematic in terms of the management of such a radioisotope or internal exposure. Moreover, PET has been known to have low spatial resolution.

On the other hand, MRI is a technique of applying a nuclear magnetic resonance (NMR) phenomenon to computed tomography, and thus, it is considered that MRI does not cause radiation exposure, differing from X-ray CT or PET. Moreover, MRI has been known to have higher tissue-specificity, compared with other modalities such as X-ray CT.

In general, in MRI examination/diagnosis, two different types of image data, namely, a T1-weighted image (mainly, an image created from a nuclear magnetization distribution contrasted with longitudinal relaxation) and a T2-weighted image (mainly, an image created from a nuclear magnetization distribution contrasted with transverse relaxation), with respect to the state of protons (hydrogen nuclei) included in the unit area as a subject (longitudinal relaxation or T1 relaxation, and transverse relaxation or T2 relaxation), are obtained, while adjusting parameter values such as echo time (TE) and repetition time (TR), and the obtained images are then analyzed. For every state of protons in the observed tissue, organ or the like, a T1-weighted image and/or a T2-weighted image each having different image contrast are obtained. Usually, such images are processed into and/or outputted as monochrome images having contrasting density.

When a T1 value (T1 relaxation time) is measured, the shorter the time, the whiter the color that can be obtained (becomes higher signals), and the longer the time, the blacker the color that can be obtained (becomes lower signals), so that the color can be contrasted to create an image (T1-weighted image). On the other hand, when a T2 value (T2 relaxation time) is measured, the longer the time, the whiter the color that can be obtained (becomes higher signals), and the shorter the time, the blacker the color that can be obtained (becomes lower signals), so that the color can be contrasted to create an image (T2-weighted image).

Moreover, for the purpose of further increasing the contrast and tissue-specificity of MRI images in the MRI examination/diagnosis, various contrast agents have been developed.

Typical contrast agents are, for example, gadolinium complexes such as Gd-DTPA (gadolinium-diethylenetri-aminepentaacetic acid), which have an action to reduce the T1 relaxation time and increase the contrast (signal intensity) in a T1-weighted image.

Gd-DTPA is used, for example, in detection of glioma. Since Gd-DTPA is chelated, the side effects thereof are reduced compared with a free gadolinium. However, Gd-DTPA still has side effects such as allergic reaction, liver toxicity or renal toxicity. In addition, since Gd-DTPA does not have site-specificity (e.g., tumor selectivity), a large amount of Gd-DTPA has needed to be administered in order to, for example, clarify the contrast between a tumor and other tissues (Patent Literature 1).

However, there have been no alternatives to the conventional methods or contrast agents. Accordingly, it has been desired for many years to develop a novel diagnostic agent and a novel diagnostic method.

CITATION LIST

Patent Literature

[Patent Literature 1] International Publication No. WO 2009/157561

SUMMARY OF INVENTION

Technical Problem

It is an object of the present invention to provide a nuclear magnetic resonance diagnostic agent having reduced toxicity on a living body, causing fewer side effects and having site-specificity to a specific cell, tissue or organ, etc.

Solution to Problem

Protoporphyrin IX (hereinafter also referred to as "PpIX") has been known as a precursor for pigments such as heme and chlorophyll, and this precursor has been known to have the property of being site-specifically accumulated, for example, in cancer tissues. On the other hand, 5-aminolevulinic acid (hereinafter also referred to as "ALA") and a derivative thereof have been known as intermediates of pigment biosynthetic pathways, and it has been known that ALA and a derivative thereof are metabolically activated to PpIX in a cell by the activation of a series of enzyme groups in a heme biosynthetic pathway (for example, Japanese Patent Laid-Open No. 2011-26221 and Japanese Patent No. 2731032).

The present inventors have conducted intensive studies. As a result, the inventors have focused on a phenomenon in which metabolites of ALA or a derivative thereof administered into a living body (in particular, PpIX) are accumulated in a specific cell, tissue or organ, etc., and they have then analyzed a site in which the metabolites would be accumulated after administration of ALA to the living body, utilizing nuclear magnetic resonance. As a result, the present inventors have surprisingly found that ALA and a derivative thereof are useful as diagnostic agents for solving the aforementioned problem, thereby completing the present invention. To date, an example of combining administration of ALA or a derivative thereof to a living body with a nuclear magnetic resonance method has not yet been reported.

Specifically, the object of the present invention can be achieved by providing a nuclear magnetic resonance diagnostic agent containing a compound represented by the following formula (I) or a salt thereof:

[Formula 1]

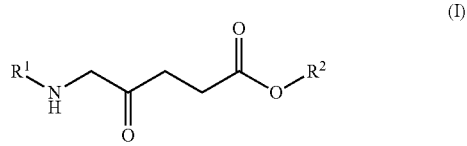
(I)

wherein $R^1$ represents a hydrogen atom or an acyl group, and $R^2$ represents a hydrogen atom, a linear or branched alkyl group, a cycloalkyl group, an aryl group, or an aralkyl group.

In addition, in one aspect of the nuclear magnetic resonance diagnostic agent of the present invention, $R^1$ and $R^2$ preferably each represent a hydrogen atom.

Moreover, in one aspect, the nuclear magnetic resonance diagnostic agent of the present invention is preferably a contrast agent used in MRI.

Furthermore, in one aspect, the nuclear magnetic resonance diagnostic agent of the present invention preferably increases the contrast of a T2-weighted image, utilizing nuclear magnetic resonance.

Further, in one aspect, the nuclear magnetic resonance diagnostic agent of the present invention is preferably used to diagnose a disease or a condition selected from the group consisting of neoplastic diseases, infectious diseases, inflammatory diseases, autoimmune diseases, demyelinating diseases, metabolic diseases, degenerative diseases, vascular disorders, and injuries.

Further, in one aspect, the nuclear magnetic resonance diagnostic agent of the present invention preferably further contains one or two or more metal-containing compounds.

Still further, in one aspect, the nuclear magnetic resonance diagnostic agent of the present invention preferably contains an iron-containing compound as the metal-containing compound.

In another aspect, the present invention provides a method for detecting a condition of a cell, tissue or organ in a subject, the method comprising a step of detecting the condition of a cell, tissue or organ in a subject to which a compound represented by the following formula (I) or a salt thereof has been administered, utilizing nuclear magnetic resonance:

[Formula 2]

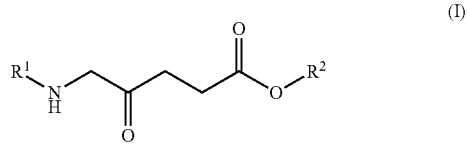
(I)

wherein $R^1$ represents a hydrogen atom or an acyl group, and $R^2$ represents a hydrogen atom, a linear or branched alkyl group, a cycloalkyl group, an aryl group, or an aralkyl group.

In another aspect, the present invention provides a method for diagnosing a condition of a cell, tissue or organ in a subject, comprising:

(a) a step of administering to a subject, a compound represented by the following formula (I) or a salt thereof:

[Formula 3]

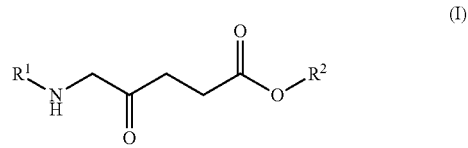
(I)

wherein $R^1$ represents a hydrogen atom or an acyl group, and $R^2$ represents a hydrogen atom, a linear or branched alkyl group, a cycloalkyl group, an aryl group, or an aralkyl group;

(b) a step of detecting the condition of the cell, tissue or organ in the subject, utilizing nuclear magnetic resonance; and (c) a step of diagnosing the condition of the cell, tissue or organ in the subject, based on the detection results.

In addition, in one aspect of the method for diagnosing a condition of a cell, tissue or organ in a subject of the present invention, the cell, tissue or organ in the subject is preferably a site in which the metabolite of the compound represented by the above formula (I) or a salt thereof is accumulated.

Moreover, in one aspect of the method for diagnosing a condition of a cell, tissue or organ in a subject of the present invention, the cell, tissue or organ in the subject is preferably a tumor, that is, a site in which a metabolite of the compound represented by the above formula (I) or a salt thereof is accumulated.

In another aspect, the present invention provides a method for obtaining a T2-weighted image in which the contrast is increased in MRI, comprising:

(1) a step of administering to a subject, a compound represented by the following formula (I) or a salt thereof:

[Formula 4]

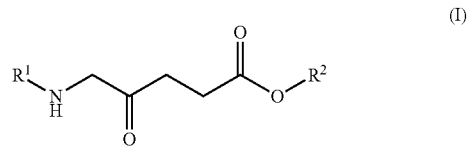
(I)

wherein $R^1$ represents a hydrogen atom or an acyl group, and $R^2$ represents a hydrogen atom, a linear or branched alkyl group, a cycloalkyl group, an aryl group, or an aralkyl group;

(2) a step of applying MRI to the subject, utilizing nuclear magnetic resonance; and (3) a step of obtaining a T2-weighted image in the subject.

Needless to say, any given combination of one or more characteristics of the present invention, as described above, is also included in the present invention, as appropriate.

Advantageous Effects of Invention

Using the nuclear magnetic resonance diagnostic agent of the present invention, it becomes possible to further reduce toxicity on a living body and side effects, and also to site-specifically detect or diagnose a condition of a cell, tissue or organ in a subject, and the like.

BRIEF DESCRIPTION OF DRAWINGS

FIG. 1A relates to an image obtained by 2D-RARE, which is shown as a reference image. It is to be noted that, for example, in FIG. 1A, the letter A indicates that it is a front portion in the direction in a gantry.

FIG. 1B relates to a parametric image regarding T1 saturation recovery.

FIG. 1C relates to a parametric image regarding T2 relaxation.

FIG. 1D relates to an image obtained by 2D-RARE, which is shown as a reference image.

All of FIGS. 1A to 1C are images of the section of an identical tumor portion sample collected from an ALA administration group. FIG. 1D shows an image of the section of a tumor portion sample collected from a control group.

FIG. 2A relates to a T2-weighted image in an ALA administration group. The region enclosed by a white circle indicates a part of the section of a transplanted tumor portion, and it corresponds to the ROI region set in FIG. 1. The region enclosed by a white square indicates a part of the section of non-tumor tissues (skin tissues, etc.) derived from a rat, into which tumor cells have been transplanted. The black arrow indicates that although it is the section of a tumor portion in the ALA administration group, the peripheral portion of the section of the tumor portion was observed in a high signal zone in a circle portion in a dark image (at low signals) in the T2-weighted image.

FIG. 2B relates to a T1-weighted image in an ALA administration group.

FIG. 2C relates to a T2-weighted image in a control group. The region enclosed by a white circle indicates a part of the section of a transplanted tumor portion. The region enclosed by a white square indicates a part of the section of non-tumor tissues (skin tissues, etc.) derived from a rat, into which tumor cells have been transplanted. The region enclosed by a black triangle indicates a part of the section of rough connective tissues that are present between skin tissues derived from a rat, into which tumor cells have been transplanted, and the tumor cells.

FIG. 2D relates to a T1-weighted image in a control group.

FIG. 3A and FIG. 3C relate to T2-weighted images obtained by imaging different slice surfaces of tissues collected from the ALA administration group.

FIG. 3B and FIG. 3D relate to T2-weighted images obtained by imaging different slice surfaces of tissues collected from the control group.

DESCRIPTION OF EMBODIMENTS

Figure 1:
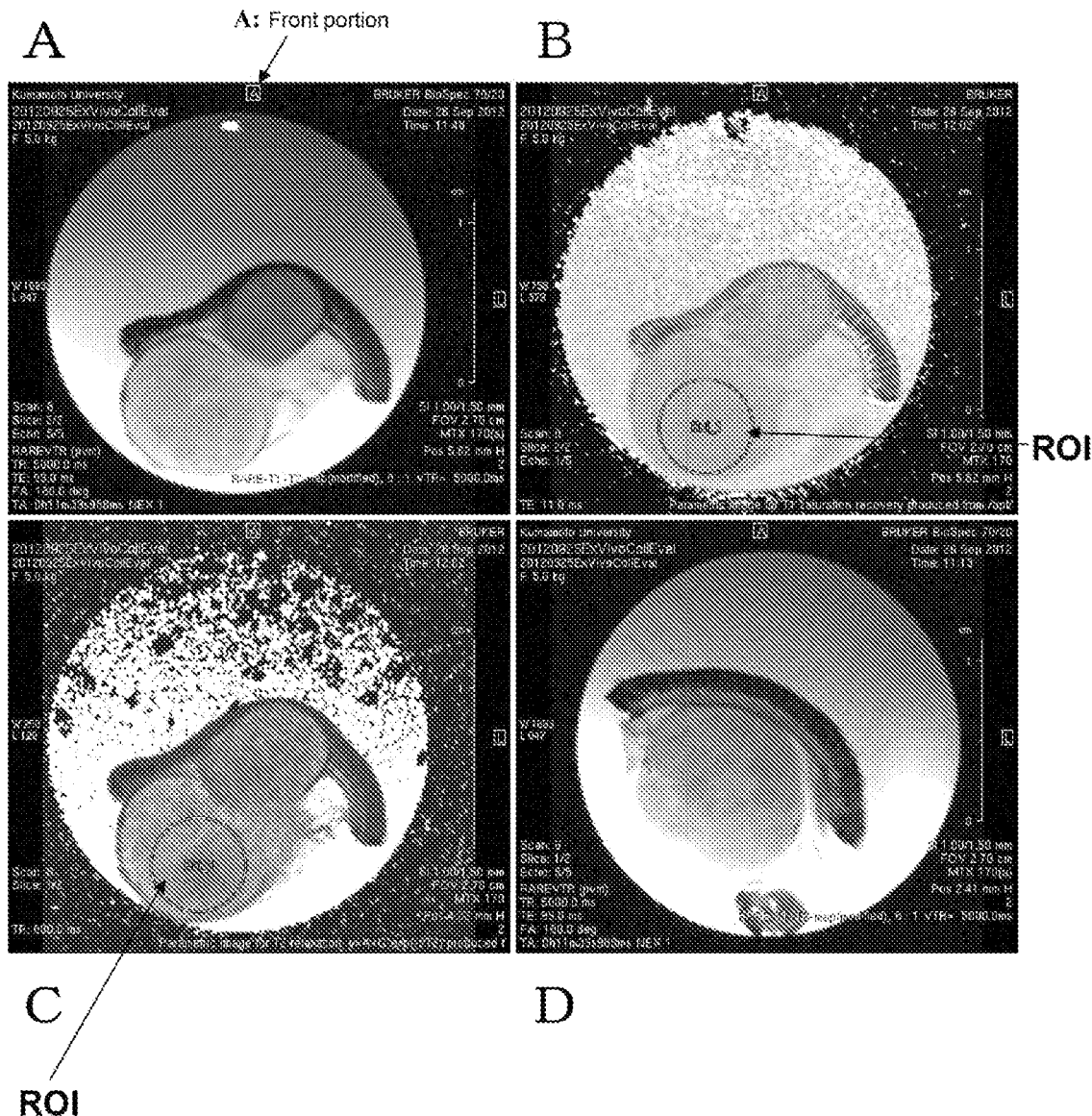
FIG. 1 is a view showing an example of the setting of ROI used in the measurement of T1 value/T2 value in a tumor portion collected from an ALA administration group, with regard to an image obtained by an MRI apparatus.

It has been reported that ALA or a derivative thereof is safe to living bodies (for example, J Endourol. 2009 Sep. 23 (9), pp. 1387-94; Urology. 2008 August 72 (2), pp. 345-8, Epub 2008 Apr. 11; Br J Cancer. 2001 Jan. 5 84 (1), pp. 33-7). Accordingly, the nuclear magnetic resonance diagnostic agent of the present invention has reduced toxicity on a living body and causes fewer side effects, when compared with conventional in vivo diagnostic agents (for example, gadolinium contrast agents or radioisotopes).

The compound contained as an active ingredient in the nuclear magnetic resonance diagnostic agent of the present invention is ALA or a derivative thereof, or a salt thereof, and the compound represented by the above formula (I) or a salt thereof (hereinafter, they are also referred to as "ALA member(s)", collectively) can be shown as examples. ALA that is also referred to as δ-aminolevulinic acid is one of amino acids, wherein $R^1$ and $R^2$ in the above formula (I) each represent a hydrogen atom. The ALA derivative may be a compound other than ALA, wherein $R^1$ in the above formula (I) represents a hydrogen atom or an acyl group and $R^2$ in the above formula (I) represents a hydrogen atom, a linear or branched alkyl group, a cycloalkyl group, an aryl group, or an aralkyl group.

The acyl group in the above formula (I) is not limited. Examples of the acyl group may include: a linear or branched alkanoyl group having 1 to 8 carbon atoms, such as formyl, acetyl, propionyl, butyryl, isobutyryl, valeryl, isovaleryl, pivaloyl, hexanoyl, octanoyl and benzylcarbonyl groups; and an aroyl group having 7 to 14 carbon atoms, such as benzoyl, 1-naphtoyl and 2-naphthoyl groups.

The alkyl group in the above formula (I) is not limited. Examples of the alkyl group may include: a linear or branched alkyl group having 1 to 8 carbon atoms, such as methyl, ethyl, propyl, isopropyl, butyl, isobutyl, sec-butyl, tert-butyl, pentyl, isopentyl, neopentyl, hexyl, heptyl and octyl groups.

The cycloalkyl group in the above formula (I) is not limited. Examples of the cycloalkyl group may include: a saturated or optionally partially unsaturated cycloalkyl group having 3 to 8 carbon atoms, such as cyclopropyl, cyclobutyl, cyclopentyl, cyclohexyl, cycloheptyl, cyclooctyl, cyclododecyl and 1-cyclohexenyl groups.

The aryl group in the above formula (I) is not limited. Examples of the aryl group may include: an aryl group having 6 to 14 carbon atoms, such as phenyl, naphthyl, anthryl and phenanthryl groups.

The aralkyl group in the above formula (I) is not limited. The same groups as those for the above described aryl group can be exemplified as an aryl portion of the aralkyl group, and the same groups as those for the above described alkyl group can be exemplified as an alkyl portion of the aralkyl group. Specific examples may include an aralkyl group having 7 to 15 carbon atoms, such as benzyl, phenethyl, phenylpropyl, phenylbutyl, benzhydryl, trityl, naphthylmethyl and naphthylethyl groups.

The above described ALA derivative is not limited. In one embodiment, a compound wherein the above $R^1$ represents a formyl, acetyl, propionyl or butyryl group, etc., and a compound wherein the above $R^2$ represents a methyl, ethyl, propyl, butyl or pentyl group, etc. are preferable. Moreover, in a specific embodiment, a compound wherein a combination of the above $R^1$ and the above $R^2$ is formyl and methyl, acetyl and methyl, propionyl and methyl, butyryl and methyl, formyl and ethyl, acetyl and ethyl, propionyl and ethyl, or butyryl and ethyl, is preferable, but examples of the compound are not limited thereto.

Depending on administration aspect, an ALA member may be administered, for example, in the form of various salts, esters, or prodrugs (precursors) that are decomposed by enzymes in living bodies, in order to increase the solubility thereof. Examples of the salt of ALA or a derivative thereof may include pharmacologically acceptable acid addition salts, metal salts, ammonium salts, and organic amine addition salts. Examples of the acid addition salts may include: various inorganic acid salts such as hydrochloride, hydrobromide, hydroiodide, phosphate, nitrate and sulfate; and various organic acid addition salts such as formate, acetate, propionate, toluenesulfonate, succinate, oxalate, lactate, tartrate, glycolate, methanesulfonate, butyrate, valerate, citrate, fumarate, maleate and malate. Examples of the metal salts may include: various alkaline metal salts such as lithium salts, sodium salts, and potassium salts; various alkaline-earth metal salts such as magnesium salts and calcium salts; and various metal salts such as aluminum and zinc. Examples of the ammonium salts may include alkyl ammonium salts such as ammonium salts and tetramethylammonium salts. Examples of the organic amine salts may include various salts such as triethylamine salts, piperidine salts, morpholine salts and toluidine salts. It is to be noted that these salts can also be used in the form of a solution upon the use thereof.

Among the aforementioned ALA members, preferred examples include: ALA; various esters such as ALA methyl ester, ALA ethyl ester, ALA propyl ester, ALA butyl ester and ALA pentyl ester; and hydrochlorides, phosphates, and sulfates thereof. Among others, ALA hydrochloride and ALA phosphate are more preferable.

The ALA members can be produced by known methods such as chemical synthesis, production using microorganisms, and production using enzyme. In addition, the ALA members may also form a hydrate or a solvate. Moreover, the ALA members can be used alone or by appropriately combining two or more types of ALA.

In one aspect, the nuclear magnetic resonance diagnostic agent of the present invention may comprise a metal-containing compound, as long as it does not cause unacceptable adverse effects on living bodies and the like and the object and problem of the present invention can be achieved. A metal portion in such a metal-containing compound is not limited, and examples of such a metal portion may include iron, magnesium, zinc, nickel, vanadium, cobalt, copper, chromium, and molybdenum. A person skilled in the art could appropriately select a suitable dose of the metal-containing compound and could administer such a suitable dose of metal-containing compound, together with the ALA member, to a subject.

It has been known that when an image is obtained by a nuclear magnetic resonance imaging (MRI) apparatus, the T2 relaxation time is generally decreased by metal in a living body.

As described above, PpIX is a precursor of a heme pigment. Thus, if iron is administered, together with the ALA member, to a living body, PpIX that is a metabolite of the ALA member, which is selectively accumulated in a specific site in the living body, is further metabolized to heme. In such a case, by using an iron compound in combination, accumulation of metabolites of the ALA member (in particular, PpIX) in normal tissues is suppressed by further metabolism to heme. On the other hand, in stomach cancer cells and the like in which metabolites of the ALA member (in particular, PpIX) are easily accumulated, accumulation of sufficient amounts of metabolites of the ALA (in particular, PpIX) can be retained. Accordingly, by administering an iron compound in combination with the ALA member, it becomes possible, for example, to increase the signal to noise ratio (S/N ratio), with regard to an image contrast difference between normal tissues and tumor tissues in the T2-weighted image obtained by MRI. Therefore, in one aspect, the nuclear magnetic resonance diagnostic agent of the present invention may preferably contain an iron-containing compound, as long as it does not cause unacceptable adverse effects on living bodies and the like and the object and problem of the present invention can be achieved.

The above described iron compound may be either an organic salt or an inorganic salt. The inorganic salt is not limited, and examples of the inorganic salt may include ferric chloride, iron sesquioxide, ferrous sulfate and ferrous pyrophosphate. The organic salt is not limited, and examples of the organic salt may include: carboxylic acid salts, for example, citric acid salts that are hydroxycarboxylic acid salts, such as ferrous citrate, sodium iron citrate, sodium ferrous citrate, and ammonium iron citrate; organic acid salts such as ferric pyrophosphate, iron lactate, ferrous gluconate, sodium iron diethylenetriaminepentaacetate, ammonium iron diethylenetriaminepentaacetate, sodium iron ethylenediaminetetraacetate, ammonium iron ethylenediaminepentaacetate, sodium iron dicarboxymethyl glutamate, ammonium iron dicarboxymethyl glutamate, ferrous fumarate, ferrous acetate, iron oxalate, ferrous succinate and sodium iron citrate succinate; and heme iron, dextran iron, triethylenetetramine iron, lactoferrin iron, transferrin iron, iron chlorophyllin sodium, ferritin iron, saccharated iron oxide, and ferrous glycine sulphate.

In one embodiment, the dose of the above described iron-containing compound is not limited with respect to the dose of the ALA member (in ALA conversion). The iron-containing compound may be administered at a molar ratio of 0.01:1 to 100:1, preferably of 0.05:1 to 10:1, and more preferably of 0 1:1 to 8:1, with respect to the ALA member. A person skilled in the art could appropriately select a suitable dose of the iron-containing compound and could administer such a suitable dose of the iron-containing compound, together with ALA, to a subject. Also, with regard to the doses of metal-containing compounds other than the iron-containing compound, such a skilled person could appropriately determine them, in light of the object and problem of the present invention.

In one aspect, the ALA member and a metal-containing compound, which are comprised in the nuclear magnetic resonance diagnostic agent of the present invention, can be administered in the form of a composition comprising both the ALA member and the metal-containing compound, or each alone. When the ALA member and the metal-containing compound are administered each alone, it is preferable that they be administered simultaneously. Herein, the term "simultaneously" means not only that administration is performed at the same time, but it also means that although administration is not performed at the same time, it is performed without having considerable intervals so that the administration of ALA member and the metal-containing compound provides an added effect, and preferably a synergistic effect.

The nuclear magnetic resonance diagnostic agent of the present invention may be used, not be particularly limited, as long as it utilizes a nuclear magnetic resonance phenomenon. Preferably, the nuclear magnetic resonance diagnostic agent of the present invention may be used in an MRI apparatus, an MRS (magnetic resonance spectroscopy) apparatus, an NMR apparatus, and the like. In addition, these apparatuses may be used based on findings known to a person skilled in the art, depending on the purpose of the present invention. For instance, the nuclear magnetic resonance imaging (MRI) method is suitable for the analysis of anatomical information. On the other hand, the MRS method is one of imaging methods carried out in MRI, and this method is excellent in terms of the analysis of chemical information of metabolic substances. In the present invention, the "nuclear magnetic resonance diagnostic agent" is not limited, as long as it is an agent or a composition that utilizes the principles of a nuclear magnetic resonance phenomenon and can be applied to diagnostic purpose. For example, in one aspect, the nuclear magnetic resonance diagnostic agent of the present invention can be understood to be an agent, a drug or a composition utilized in: detection or analysis of the dynamic condition (distribution) or localization, etc. of the ALA member and a metabolite thereof in a subject; detection of the clinical and pharmacological characteristics of cells, tissues or organs in a subject, or clinical or pharmacological diagnosis thereof; detection of information serving as an indicator for identifying a disease or a condition, or identification or diagnosis of a disease or a condition; detection, identification or diagnosis of the shape or position of a disease or a condition; confirmation of therapeutic effects (for example, confirmation of therapeutic effectiveness after administration of an anticancer agent, etc.); combined diagnosis upon the surgical operation; and the like. For example, when the nuclear magnetic resonance diagnostic agent of the present invention is used in MRI examination/diagnosis, it can be used as a contrast agent (which indicates an agent or a composition administered to a living body in order to emphasize in obtaining an image contrast in the MRI image, for example, in a specific cell, tissue or organ, etc. in the living body). For example, when the nuclear magnetic resonance diagnostic agent of the present invention is used in MRS detection/diagnosis, it can be used as an agent, a drug or a composition that is administered to a living body in order to change a waveform pattern measured by the MRS apparatus, with regard to a specific cell, tissue or organ, etc. in the living body.

As an MRI apparatus, an apparatus using a superconducting electromagnet, a permanent magnet or the like has been known. The MRI apparatus using a superconducting electromagnet generates a strong magnetic field, so as to configure a precise, high contrast image. In the case of the MRI apparatus using a superconducting electromagnet, the subject to be imaged (e.g., a human, etc.) is not limited, as long as it is acceptable. For example, the subject to be imaged may be a subject having a magnetic field such as 10, 9.4, 8, 7, 6, 5, 4, 3, 2, 1.5, 1 or 0.5 tesla. In one embodiment, a low magnetic field is preferable from the viewpoint of costs, simplicity and the like, and a high magnetic field is preferable from the viewpoint of spatial resolution and the like.

The nuclear magnetic resonance imaging method (MRI) is not limited. As such a nuclear magnetic resonance imaging method (MRI), various methods such as a spin echo method (SE), a gradient echo method (GRE), an echo planar method (EPI), proton density-weighted imaging, a flare method (FLAIR; fluid attenuated inversion recovery), diffusion weighted imaging (DWI), a fat suppression method, and a RARE method (Rapid Acquisition with Relaxation Enhancement) have been known to a person skilled in the art. All of these methods can be used for the nuclear magnetic resonance diagnostic agent of the present invention. A person skilled in the art could understand that, in light of the object and problem of the present invention, a suitable method can be appropriately selected, and an optimal MRI contrast images (a T1-weighted image, and particularly, a T2-weighted image) can be obtained. For example, when the ALA member is used as a contrast agent, the contrast of a T2-weighted image is increased in the site-specifically accumulated sites (e.g. tumor tissues, etc.) of ALA member metabolites (in particular, PpIX), compared with the case of not administering the ALA member, and the accumulated site is outputted as a white portion (becomes high signals) (in other words, the T2 relaxation time is prolonged). In order to further increase such a contrast difference, TR, TE, a magnetic field and the like may be adjusted, so that the image contrast may be optimized.

In one embodiment, when the nuclear magnetic resonance diagnostic agent of the present invention comprising the ALA member is used as an MRI contrast agent, it is preferable that the T2 relaxation time be significantly prolonged, in particular, in tumor tissues and the like, compared to the case of not administering the ALA member, although the embodiment is not limited thereto. For example, the T2 relaxation time is more preferably prolonged at a magnification of 1.1 to 10 times or more (for example, 1.2 to 5 times or more).

The administration route of the nuclear magnetic resonance diagnostic agent of the present invention to a subject (a living body, etc.) may be either systemic administration or local administration. Examples of the administration route of the present nuclear magnetic resonance diagnostic agent may include, but are not limited to, oral administration including sublingual administration, and parenteral administration such as inhalation administration, direct administration to target tissues or organs, which uses a catheter, intravenous administration including infusion, transdermal administration using a poultice and the like, and administration involving forcing enteral nutrition, which uses suppositories, a nasogastric tube, a nasal intestinal tube, a gastrostomy tube or a jejunostomy tube.

The dosage form of the nuclear magnetic resonance diagnostic agent of the present invention is not limited, and it may be appropriately determined depending on the above described administration route. Examples of the dosage form may include an injection, drops, a tablet, a capsule, fine granules, a powder agent, a liquid agent, a water agent dissolved in syrup or the like, a poultice, and a suppository.

For preparation of the nuclear magnetic resonance diagnostic agent of the present invention, for example, pharmacologically acceptable carriers, excipients, diluents, additives, disintegrators, binders, coating agents, lubricating agents, gliding agents, lubricants, flavors, sweeteners, solubilizers, solvents, gelling agents, nutrients, and the like may be added, as necessary. Further, addition of these agents may have an effect on the absorbency and blood concentration of the nuclear magnetic resonance diagnostic agent of the present invention, and may result in a change in the in vivo kinetics thereof. Specific examples of the aforementioned agents may include water, saline, animal fats and oils, vegetable oils, lactose, starch, gelatin, crystalline cellulose, rubber, talc, magnesium stearate, hydroxypropyl cellulose, polyalkylene glycol, polyvinyl alcohol, and glycerin. When the nuclear magnetic resonance diagnostic agent of the present invention is prepared in the form of an aqueous solution, in order to prevent the decomposition of the ALA member, attention should be paid to prevent the aqueous solution from being converted to an alkaline solution. If the aqueous solution is converted to an alkaline solution, the decomposition can also be prevented by removing oxygen.

When the nuclear magnetic resonance diagnostic agent of the present invention is administered to a subject, the applied dose to the subject, timing, frequency and period may be different depending on the age and body weight of the subject, or the condition of a cell, tissue or organ in the subject to be detected, identified or diagnosed, etc., or the symptom, condition or the like in the subject to be detected, identified or diagnosed.

The subject to which the nuclear magnetic resonance diagnostic agent of the present invention is administered (applied) is not limited. Examples of the subject may include mammals (humans, non-human mammals (e.g., a mouse, a rat, a dog, a cat, a rabbit, a bovine, a horse, a sheep, a goat, a swine, etc.), or non-mammals (e.g., fish, reptiles, amphibian or avian)), plants, insects, bacteria, and cells (including cultured cells), tissues and organs, etc., which are derived from these organisms. Alternatively, the subject may also be an artificial environment (e.g., an in vitro reaction system, etc.). The subject used in the present invention is preferably a mammal, and particularly preferably a human.

For example, by utilizing a phenomenon in which approximately 2 hours after administration of the ALA member to a human, or a rodent such as a mouse or a rat, PpIX that is a metabolite of the ALA member is site-specifically sufficiently accumulated in a target site (for example, a tumor site), the dose of the ALA member, timing, frequency, period and the like may be adjusted, as appropriate. The target site may be a site (tissues, organs, etc.) in a subject, in which metabolites of the administered ALA member (in particular, PpIX) are accumulated.

In one aspect, when the subject is a human, for example, the dose of the ALA member per adult may be 0.1 mmol to 120 mmol/day, preferably 0.2 mmol to 90 mmol/day, more preferably 0.3 mmol to 60 mmol/day, and further preferably 0.35 mmol to 40 mmol/day, in terms of the mole of ALA. Also in cases of using the other ALA member, a preferred dose can be calculated by conversion to moles. In addition, local administration would require a smaller amount of the ALA member than the case of systemic administration.

Examples of the administration frequency of the ALA member may include administration once or several times per day, and continuous administration involving infusions and the like. In order to perform precise detection or diagnosis using the ALA member as a diagnostic agent, it is preferable that, after the administered ALA member or metabolites generated as a result of the administration of the ALA member have been completely metabolized and/or decomposed in a living body, the next ALA member be administered, as necessary.

Taking into consideration a symptom, a condition or the like in a subject to be detected or diagnosed, for example, the administration period of the ALA member can be determined by a method that has been conventionally known to pharmacologists or clinicians in the technical field, based on various clinical guidelines and the like.

After administration of the ALA member to a subject, the accumulation (amount) of metabolites of the ALA member (in particular, PpIX) in a desired cell, tissue or organ in the subject reaches a peak in approximately 2 hours, and thereafter, the peak accumulation (amount) is maintained for several hours (e.g., 8 hours) and then decreased. This behavior can be confirmed by observing the fluorescent intensity of PpIX in the living body. Accordingly, in one embodiment, for example, 1 to 24 hours, preferably 1.5 to 15 hours, and more preferably 2 to 8 hours after the nuclear magnetic resonance diagnostic agent of the present invention comprising the ALA member has been administered to a subject, the condition of a desired cell, tissue or organ in the subject may be detected or diagnosed, using an MRI apparatus, an MRS apparatus, an NMR apparatus or the like, although the embodiment is not limited thereto. A person skilled in the art could understand that, taking into consideration the time at which metabolites of the ALA member arrive at a desired cell, tissue, organ, etc. in the subject, the accumulation time, the time at which the metabolites of the ALA member are saturated (reach a peak) in the desired cell, tissue or organ, and the like, an optimal measurement timing can be determined, as appropriate. Preferably, the site in which the metabolites of the administered ALA members are accumulated may be specified by imaging a cell, tissue or organ in a subject, using the nuclear magnetic resonance diagnostic agent of the present invention as an MRI contrast agent, and then obtaining an image data (in particular, a T2-weighted image data in which the contrast is increased).

Accordingly, in one embodiment, the nuclear magnetic resonance diagnostic agent of the present invention may be used for detection (in the present invention, the detection means, for example, that the condition is detected as (a signal intensity) in) an image utilizing an MRI apparatus, or that the condition is detected as a waveform utilizing an MRS apparatus, etc.), diagnosis, and the like of the condition of a cell, tissue or organ in a subject, in which the principles of nuclear magnetic resonance are utilized. The present invention may be carried out according to any one or an appropriate combination of several aspects selected from all the aspects described in the present description, unless they are technically inconsistent with one another.

In one embodiment, the nuclear magnetic resonance diagnostic agent of the present invention may be used for, but not limited to, the detection, diagnosis, analysis, combined use with surgical operation, etc. of a disease or a condition, such as neoplastic disease, infectious disease, inflammatory disease, autoimmune disease, demyelinating disease, metabolic disease, degenerative disease, vascular disorder, and injury. The above described disease or condition is preferably a disease or a condition selected from the group consisting of neoplastic disease, degenerative disease, inflammatory disease, autoimmune disease, and demyelinating disease, and is more preferably a disease or a condition selected from the group consisting of neoplastic diseases and degenerative diseases, although the embodiment is not limited thereto. Moreover, in one embodiment, the nuclear magnetic resonance diagnostic agent of the present invention is preferably used as an MRI contrast agent for the detection, diagnosis, etc. of these diseases or conditions.

With regard to the above described neoplastic disease, examples of the tumor may include, but are not limited to, benign tumors such as hemangioma, adenoma, papilloma, polyp, cystadenomas, fibroma, myxoma, lipoma, osteoma, chondroma, leiomyoma, and rhabdomyoma, or primary or metastatic, and invasive or non-invasive cancer, sarcoma and the like, including brain tumor, spinal cord tumor, maxillary carcinoma of antral origin, pancreatic juice adenocarcinoma, carcinoma of gingiva, tongue cancer, lip cancer, nasopharyngeal cancer, oropharynx cancer, hypopharynx cancer, laryngeal cancer, thyroid cancer, parathyroid cancer, lung cancer, pleural tumor, cancer sexual peritonitis, carcinomatous pleuritis, esophageal cancer, stomach cancer, colon cancer, bile duct cancer, gallbladder cancer, pancreatic cancer, liver cancer, kidney cancer, bladder cancer, prostate cancer, penile cancer, testicular tumor, adrenal cancer, cervical cancer, endometrial cancer, vaginal cancer, vulvar cancer, ovarian cancer, bone tumor, breast cancer, skin cancer, melanoma, basal cell carcinoma, leukemia, lymphoma, Hodgkin's disease, plasmacytoma, osteosarcoma, chondrosarcoma, liposarcoma, rhabdomyosarcoma, and fibrosarcoma. Preferred examples of the above described tumor include, but are not limited to, brain tumor, spinal cord tumor (e.g., glioma such as glioblastoma), and hemangioma. The brain tumor may also be a metastatic brain tumor.

The above described infectious disease is not particularly limited, as long as it is a disease or a condition, such as bacterial infection, fungal infection, or viral infection, which is developed by the entering of virus, *mycoplasma*, bacteria, parasites, etc. into a body. Specific examples of the above described infectious disease may be the same as those as listed for the following inflammatory disease.

Examples of the above described inflammatory disease include, but are not limited to, meningitis, encephalitis, rhinitis, sinusitis, pharyngitis, laryngitis, orbital cellulitis, epiglottitis, retropharyngeal abscess, subacute thyroiditis, Lemierre's syndrome, pneumonia, bronchitis, tuberculosis, infective endocarditis, pericarditis, myocarditis, infectious aortitis, sepsis, cholecystitis, cholangitis, hepatitis, liver abscess, pancreatitis, splenic abscess, gastritis and/or gastric ulcer, enteritis, appendicitis, iliopsoas abscess, urinary organ, pyelonephritis, cystitis, prostatitis, vaginitis, pelvic infections, infectious arthritis, osteomyelitis, fasciitis, myositis, and lymphadenitis. Preferred examples of the above described inflammatory disease include, but are not limited to, encephalitis and meningitis.

The above described autoimmune disease may mean a disease or a condition developed by a phenomenon in which an immune system having a role in recognizing foreign matters and eliminating them from a body excessively reacts with its own normal cells or tissues and makes an attack on them, although the definition is not limited thereto. Examples of the above described autoimmune disease may include, but are not limited to, organ-specific autoimmune diseases such as Guillain-Barre syndrome, myasthenia gravis, chronic gastritis, autoimmune hepatitis, autoimmune pancreatitis, rapidly progressive glomerulonephritis, and autoimmune optic neuropathy, or systemic autoimmune diseases such as rheumatoid arthritis, systemic lupus erythematosus, polymyositis, Sjogren's syndrome, and vasculitis syndrome.

The above described demyelinating disease is one of neurological diseases, and it may mean a disease or a condition developed by damaging the myelin sheath of myelinated nerve, although the definition is not limited thereto. Examples of the above described demyelinating disease include, but are not limited to, diseases or conditions developed in the central nervous system, such as multiple sclerosis, neuromyelitis optica (Devic's syndrome), concentric sclerosis (Balo's disease), acute disseminated encephalomyelitis (ADEM), inflammatory diffuse sclerosis (Schilder's disease), and progressive multifocal leukoencephalopathy (PML), or diseases or conditions developed in the peripheral nervous system, such as Guillain-Barre syndrome, Fisher syndrome, and chronic inflammatory demyelinating root neuritis.

The above described metabolic disease may mean a disease or a condition caused by impaired metabolism in a living body, although the definition is not limited thereto.

Examples of the above described metabolic disease include, but are not limited to, diseases or conditions caused by amino-acid metabolism abnormality, organic acid metabolism abnormality, carbohydrate metabolism abnormality, mucopolysaccharide metabolism abnormality, lipid metabolism abnormality, nucleic acid metabolism abnormality, vitamin metabolism abnormality, and the like.

The above described degenerative disease may mean a disease or a condition in which gradual degeneration is observed in nerve cells, nerve tissues and the like, although the definition is not limited thereto. Examples of the above described degenerative disease include, but are not limited to, Alzheimer's disease, Parkinson's disease, Pick's disease, Huntington's disease, amyotrophic lateral sclerosis (ALS), progressive supranuclear palsy (PSP), multiple system atrophy (MSA), and spinocerebellar degeneration (SCD).

Examples of the above described vascular disorder include, but are not limited to, cerebral vascular disorders such as cerebral infarction, cerebral hemorrhage, subarachnoid hemorrhage, chronic subdural hematoma, and acute epidural hematoma, or various peripheral vascular disorders including arteriosclerosis.

The above described injury may mean the condition of tissues, organs or the like, which are damaged by external factors, although the definition is not limited thereto. Examples of the above described injury include, but are not limited to, bleeding, bone fractures, and visceral cleft, which are caused by a physical factor, a radiation factor, a chemical factor, or the like.

In another aspect, the method for detecting a condition of a cell, tissue or organ in a subject of the present invention may be carried out according to any one or an appropriate combination of several aspects selected from all the aspects described in the present description, unless they are technically inconsistent with one another. The aforementioned method may be a method comprising a step of detecting the condition of a desired cell, tissue, organ, etc. in a subject, to which the compound represented by the above formula (I) or a salt thereof, or in some cases, the compound represented by the above formula (I) or a salt thereof and a metal-containing compound (in particular, an iron-containing compound) have been administered in detectably effective amounts. The detection is not limited, and it may be based on all types of information that can be detected utilizing the principles of nuclear magnetic resonance. Examples of the detection include: detection of the dynamic condition (distribution) of the ALA member and a metabolite thereof in a subject, and detection of localization and the like; detection of the clinical and pharmacological characteristics of a cell, tissue or organ in a subject; detection of information serving as an indicator for identifying a disease or a condition; and detection of information serving as an indicator for identifying the shape or position of a disease or a condition. The present detection method may be a non-invasive detection method. An example of the detection method is, but is not limited to, detection (for example, detection by imaging) of a site in which metabolites of the ALA member (in particular, PpIX) are accumulated, by utilizing an MRI apparatus, and using, as an indicator, an increase in the image contract in a T2-weighted image (an increase in the T2 value, namely, prolongation of the T2 relaxation time). An increase in the image contrast in the T2-weighted image (an increase in the T2 value) in a specific region of a cell, tissue or organ in a subject indicates that metabolites of the ALA member (in particular, PpIX) have been accumulated in the region. The detection may be performed in either in vivo or in vitro environment. For example, the detection may be performed on a cell, tissue, organ or the like, which has been excised from a living body after administration of ALA to the body.

In another aspect, the method for diagnosing a condition of a cell, tissue or organ in a subject of the present invention may be carried out according to any one or an appropriate combination of several aspects selected from all the aspects described in the present description, unless they are technically inconsistent with one another. The aforementioned method may comprise, for example, the following steps:

(A) a step of administering the compound represented by the above formula (I) or a salt thereof, or in some cases, the compound represented by the above formula (I) or a salt thereof and a metal-containing compound (in particular, an iron-containing compound), in diagnostically effective amounts, to a subject such as a human;

(B) a step of detecting the condition of a cell, tissue or organ in the subject, utilizing nuclear magnetic resonance; and (C) a step of diagnosing the condition of the cell, tissue or organ in the subject, based on the above described detection results.

An example of the above described step (B) is, but is not limited to, detection (for example, detection by imaging) of a site in which metabolites of the ALA member (in particular, PpIX) are accumulated, by utilizing an MRI apparatus, and using, as an indicator, an increase in the image contract in a T2-weighted image (prolongation of the T2 relaxation time). An increase in the image contrast in the T2-weighted image in a specific region of a cell, tissue or organ in a subject indicates that metabolites of the ALA member (in particular, PpIX) have been accumulated in the region. The present detection may be performed in either in vivo or in vitro environment.

The above described diagnosis in the above described step (C) may be based on all types of information that can be detected utilizing the principles of nuclear magnetic resonance, although it is not limited thereto. Examples of the diagnosis include: the analysis of the dynamic condition (distribution) of the administered ALA member and a metabolite thereof in a subject, and the analysis of localization and the like; the clinical and pharmacological diagnoses of a cell, tissue or organ in a subject; identification or diagnosis of a disease or a condition; identification or diagnosis of the shape or position of a disease or a condition; confirmation of therapeutic effects (for example, confirmation of therapeutic effectiveness after administration of an anticancer agent, etc.); and confirmation of the position or condition of a target brain tumor upon performing surgical operation on the brain tumor, with a combined use of MRI. In the above described diagnosis, for example, the accumulated site of metabolites of the ALA member (in particular, PpIX) may be compared with the non-accumulated site thereof in a single subject, or the same types of cells, tissues, organs or the like in different subjects may be compared with each other.

The above described "cell, tissue or organ in a subject" may mean all types of targets in the above described subject to be detected or diagnosed using the nuclear magnetic resonance diagnostic agent of the present invention.

In a specific embodiment, the method for detecting a condition of a cell, tissue or organ in a subject of the present invention comprises, for example, the following steps:

(O) a step of administering the compound represented by the above formula (I) or a salt thereof, or in some cases, the compound represented by the above formula (I) or a salt thereof and an iron-containing compound, in detectably effective amounts, to a subject;

(P) a step of detecting, as a first measurement value, a T2 value in the cell, tissue or organ in the subject, utilizing MRI;

(Q) a step of administering to the above described subject, a therapeutic agent (e.g., an anticancer agent, etc.) to be evaluated;

(R) a step of administering the compound represented by the above formula (I) or a salt thereof, or in some cases, the compound represented by the above formula (I) or a salt thereof and an iron-containing compound, in detectably effective amounts, to the subject; and (S) a step of detecting, as a second measurement value, a T2 value in the cell, tissue or organ in the subject, utilizing MRI, wherein when the second T2 measurement value is lower than the first T2 measurement value, it can be indicated that the above described therapeutic agent has therapeutic effects.

In this case, a step of detecting a desired number of T2 values in the cell, tissue or organ in the subject, as measurement values (a third, a forth . . . measurement values), utilizing MRI may be established between the above described step (R) and the above described step (S), and the therapeutic effects of the above described therapeutic agent may be indicated based on a fluctuation in individual T2 measurement values. Each step is desirably carried out without interfering other steps and the obtained results. In addition, a therapeutic agent that is identical to or different from the therapeutic agent used in the above described step (Q) may be administered to the subject before the above described step (O).

Moreover, the method for diagnosing a condition of a cell, tissue or organ in a subject of the present invention, which comprises a step of diagnosing the condition of the cell, tissue or organ in the subject, based on the above described detection results, may also be carried out.

In another aspect, the present invention relates to a method for obtaining a T2-weighted image in which the contrast is increased in MRI (imaging method). This method may be carried out according to any one or an appropriate combination of several aspects selected from all the aspects described in the present description, unless they are technically inconsistent with one another.

In another aspect, the present invention relates to (use of) the compound represented by the above formula (I) or a salt thereof, or in some cases, (use of) the compound represented by the above formula (I) or a salt thereof and a metal-containing compound (in particular, an iron-containing compound), for nuclear magnetic resonance diagnosis. The present invention may be carried out according to any one or an appropriate combination of several aspects selected from all the aspects described in the present description, unless they are technically inconsistent with one another.

In a further aspect, the present invention relates to use of the compound represented by the above formula (I) or a salt thereof, or in some cases, use of the compound represented by the above formula (I) or a salt thereof and a metal-containing compound (in particular, an iron-containing compound), for preparation or manufacture of a nuclear magnetic resonance diagnostic agent. The present invention may be carried out according to any one or an appropriate combination of several aspects selected from all the aspects described in the present description, unless they are technically inconsistent with one another.

It is expected that the nuclear magnetic resonance diagnostic agent of the present invention will have a high detection limit and will be a simple and commonly used agent, compared to PET.

The present inventors have surprisingly discovered that when the ALA member is administered as a contrast agent for MRI, the T2 relaxation time is significantly prolonged particularly in ROI (region of interest) in tumor tissues or the like, compared with an ALA member-non-administration group.

The previously reported contrast agents are classified into any one of the following contrast agents:

a contrast agent that reduces both the T1 relaxation time and the T2 relaxation time;

a contrast agent that reduces either one of the T1 relaxation time or the T2 relaxation time; and a contrast agent that prolongs only the T1 relaxation time (which has not yet been practically used), and thus, contrast agents that prolong the T2 relaxation time have not been known. Therefore, the ALA member is strongly expected as a contrast agent having a novel mechanism (namely, a positive contrast agent that prolongs the T2 relaxation time) for its intended use.

When a brain tumor is imaged by MRI using a gadolinium complex, the contrast of the T1-weighted image in the tumor portion can be increased by accumulation of gadolinium in the tumor as a result of the collapse of the blood brain barrier (BBB). However, such contrast effects are only additional effects. The imaged tumor portion becomes totally white on the image contrast, and thus, it does not necessarily reflect the vascular distribution condition of the brain tumor.

On the other hand, when the ALA member is used as a contrast agent, the tumor portion does not become too white on the T2-weighted image, not like the case of using a gadolinium complex, and thus, it is also possible to confirm blood vessels in the tumor. It is not only expected that the ALA member can be utilized to detect the presence of a tumor or the like on the T2-weighted image, but also that even the shape of the tumor or the like can be analyzed. Moreover, since a metabolite of the ALA member has site-specificity (for example, tumor selectivity), it is possible to administer ALA member to a subject in an amount smaller than that of a contrast agent having no site-specificity.

Furthermore, it has been known that both living tumor portions and necrotic tumor portions are often present in tumor tissues, and also that a central portion in a tumor became often necrotic due to oxygen deficiency or the like. Since metabolism actively takes place in a living tumor portion during growth, metabolites of the ALA member (in particular, PpIX) are specifically accumulated therein, and the T2 value is increased by MRI imaging (the T2 relaxation time is prolonged). On the other hand, such metabolites of the ALA member (in particular, PpIX) are (almost) never accumulated in a tumor portion that became necrotic or became nearly necrotic. Thus, in such a tumor portion that became necrotic or became nearly necrotic, the T2 value is decreased (the T2 relaxation time is reduced). Thereby, for example, in a tumor in which the central portion thereof became necrotic, the T2 value would be increased in the peripheral portion of the tumor, and the T2 value would be decreased in the central portion of the tumor. Accordingly, in one embodiment, the ALA member can also be utilized for detection, determination, etc. of the life or death of tumor cells or the activity factor of metabolism in a tumor portion, utilizing nuclear magnetic resonance.

Further, it is considered that when MRI imaging is carried out by administration of an iron compound as well as the ALA member, metabolites of the ALA member (in particular, PpIX) are not accumulated in a necrotic tumor portion in tumor tissues, or PpIX is metabolized and heme is thereby increased. Accordingly, when an iron compound as well as the ALA member is administered to a subject, an increase in the T2 value (prolongation of the T2 relaxation time) is maintained in a living tumor portion, whereas a decrease in the T2 value (reduction in the T2 relaxation time) is promoted in a necrotic tumor portion. Thus, it can be expected that an increase in the signal ratio of the T2 values in the living tumor portion/the necrotic tumor portion will be detected.

Without wishing to be bound by any theory, it is considered that when the ALA member is used as an MRI contrast agent, metabolites of the ALA member (for example, PpIX) are accumulated in the site of a tumor or the like, and bound water is changed to free water for some reason, in other words, the Hamiltonian change has effects on protons of water molecules, so that the T2 relaxation time is prolonged.

The terms used in the present description are used to explain specific embodiments, and they are not intended to limit the scope of the invention.

The term "contain" or "comprise" is used in the present description to mean that the described matter (member, step, element, number, etc.) is present, except for a case in which the two terms should be understood to have clearly different means, contextually. Thus, these terms are not intended to exclude that other matters (members, steps, elements, numbers, etc.) are present. In a case it is excluded that the above described other matters (members, steps, elements, numbers, etc.) are present, the term "consist of" may be used. The concept of the term "contain" or "comprise" encompasses the concept of the term "consist of".

Unless otherwise specified, all of the terms used herein (including technical terms and scientific terms) have the same meanings as those that are widely understood by a person skilled in the art in the technical field to which the present invention belongs. Unless another definition is clearly specified, the term used herein should be interpreted to have a meaning consistent with the meaning in the present description and the relevant technical field, and it should not be interpreted to have an ideal or excessively formal meaning.

The embodiment of the present invention is explained, while referring to a schematic view, in some cases. When such a schematic view is used, there may be a case in which it is exaggeratedly expressed in order to make clear explanation.

The terms "first", "second" and the like are used to express various elements. However, it is understood that these elements should not be limited by such terms. These terms are only used to distinguish one element from other elements. It is understood that it is possible without deviating from the scope of the present invention that, for example, a first element is described as a second element, and likewise, the second element is described as the first element, unless they are technically inconsistent with each other.

In the present description, for example, when the term "alkyl group having 1 to 8 carbon atoms" is used, a person skilled in the art could understand that this expression specifically indicates each of alkyl groups having 1, 2, 3, 4, 5, 6, 7 or 8 carbon atoms.

In the present description, all of numerical values used to indicate the contents of ingredients or the range of numerical values are interpreted to include the meaning of the term "approximately," unless otherwise specified. For example, the term "10 times" is understood to mean "approximately 10 times," unless otherwise specified.

It should be considered that all disclosures of the publications cited in the present description are incorporated into the present description. A person skilled in the art understands that relevant disclosures of such prior art publications are incorporated as portions into the present description according to the context of the present description, without deviating from the spirit and scope of the present invention.

Hereinafter, the present invention will be described more in detail with reference to the following examples. However, the present invention can be realized based on various aspects, and thus, it should not be interpreted that the present invention is limited to the following examples.

EXAMPLES

Some abbreviations used in the present Examples will be described below:
ROI: region of interest
T1: longitudinal relaxation time
T2: transverse relaxation time
T1WI: T1-weighted image
T2WI: T2-weighted image
2D-RARE: 2D-Rapid Acquisition with Relaxation Enhancement
FA: flip angle
TE: echo time
TR: repetition time
NEX: number of excitations
ETL: echo train length
FOV: field of view Brain tumor (9 L gliosarcoma: derived from Fisher 344 rat glial cells) was subcutaneously injected into the back of Fisher 344 rats (male, 8 weeks old) and was fixed therein, and the rat were then allowed to grow for 13 days (tumor diameter: approximately 1 cm). Thereafter, ALA (5-aminolevulinic acid) was administered at a dose of 100 mg/kg to each rat. Three hours after the administration of ALA, the growing tumor portion was excised, and was then preserved in a phosphate buffered saline. This sample was used as the sample group of the present invention (which is also referred to as "ALA administration group" or "ALA+").

Meanwhile, an experiment was performed in the same manner as that for the ALA administration group, with the exception that ALA was not administered. The growing tumor portion was excised, and was preserved in a phosphate buffered saline. This sample was used as a (negative) control group (which is also referred to as "ALA−").

These tumor portions, which were derived from the ALA administration group and the control group of the present invention, were each placed in a Falcon vessel with a diameter of approximately 3 cm, together with a phosphate buffered saline. Using 7T-MRI (BioSpec70/20, Bruker BioSpin GmbH, Germany) as an MRI apparatus, imaging was performed according to the 2D-RARE under the below-mentioned conditions. (It is to be noted that the 2D-RARE indicates an RARE method in which an image is obtained for 2D, namely, for every slice, and that this method is well known to a person skilled in the art.)
FA=180°
TE=11, 33, 55, 77, 99 or 100 ms
TR=5000, 3000, 1500, 800, 400 or 237 ms
NEX=1 or 5
Slice Thickness=1 mm
Spacing between slices=1.1 or 1.5 mm
Slices=2 or 9
Scan Plane=Axial
ETL=2 or 6

Pixel Bandwidth=approximately 263 or approximately 267 Hz/pix
Acquisition Matrix=128*170,192×260 or 192×520 (P×R)
Reconstruction Matrix=170×170, or 260×260
FOV=26*26 mm$^2$ or 27*27 mm$^2$ Two sections that traversed the center of a tumor were selected as sections to be imaged.

A T1 value was measured, using a saturation recovery method that utilizes a phenomenon in which if TR is changed with respect to the fixed TE using the obtained image data (DICOM format), the signal value theoretically becomes 1-exp (−TR/T1) (wherein the saturation recovery method comprises forming a non-equilibrium condition with 90° pulse and observing a process of returning to an equilibrium magnetization by applying an excitation pulse). In addition, utilizing a phenomenon in which if TE is changed with respect to the fixed TR, the signal value theoretically changes in an exponential manner (exp (−TE/T2)), a T2 value was determined.

Using these methods, the T1 value and T2 value were determined for each pixel of MRI images obtained from an ALA administration group and a control group, and thereafter, a T1 map and a T2 map were prepared from the obtained T1 and T2 values. Subsequently, a portion that could be identified as a tumor on the Magnitude image was defined as ROI and was enclosed by a circle. The average T1 value and average T2 value in the ROI enclosed by the circle, and their standard deviations were determined.

FIG. 1 illustrates an example of the setting of ROI used in the measurement of T1 value/T2 value with regard to a tumor portion collected from an ALA administration group. FIG. 1A and FIG. 1D each relate to an MRI image obtained by the 2D-RARE method, and these views are shown as reference images. FIG. 1B relates to a parametric image regarding T1 saturation recovery. FIG. 1C relates to a parametric image regarding T2 relaxation. FIG. 1A to FIG. 1C each show an image regarding the section of an identical tumor portion sample that was collected from the ALA administration group. FIG. 1D shows an image regarding the section of a tumor portion sample collected from the control group. The regions in which the ROI was set in FIG. 1B and FIG. 1C correspond to a T1 map and a T2 map, respectively. Since the image signal itself indicates a T1 value or a T2 value, it is possible to, for example, measure the T1 value or the T2 value for each pixel on these maps.

These experiments were performed independently twice, essentially under the same conditions. A plurality of measurement sites were set in the tumor portion sample collected from each of the ALA administration group and the control group, so as to enhance the reliability of the data. The results of the thus measured average T1 value and average T2 value in the ROI, and their standard deviations, are shown in Table 1.

TABLE 1

| Measurement | First average | | Second average | |
|---|---|---|---|---|
| | Average T1 value (ms) | Average T2 value (ms) | Average T1 value (ms) | Average T2 value (ms) |
| ALA+ | 2004 ± 73 | 146 ± 22 | 2188 ± 210 | 123 ± 5.7 |
| ALA− | 2074 ± 110 | 104 ± 12 | 1929 ± 36 | 96 ± 3.7 |

As a result, totally unexpectedly, it became clear that the T2 value was increased (the T2 relaxation time was prolonged) in the ALA administration group, compared to the control group. Moreover, the signal ratio (ALA administration group/control group) was approximately 1.4 times (first measurement), and approximately 1.3 times (second measurement).

Figure 2:
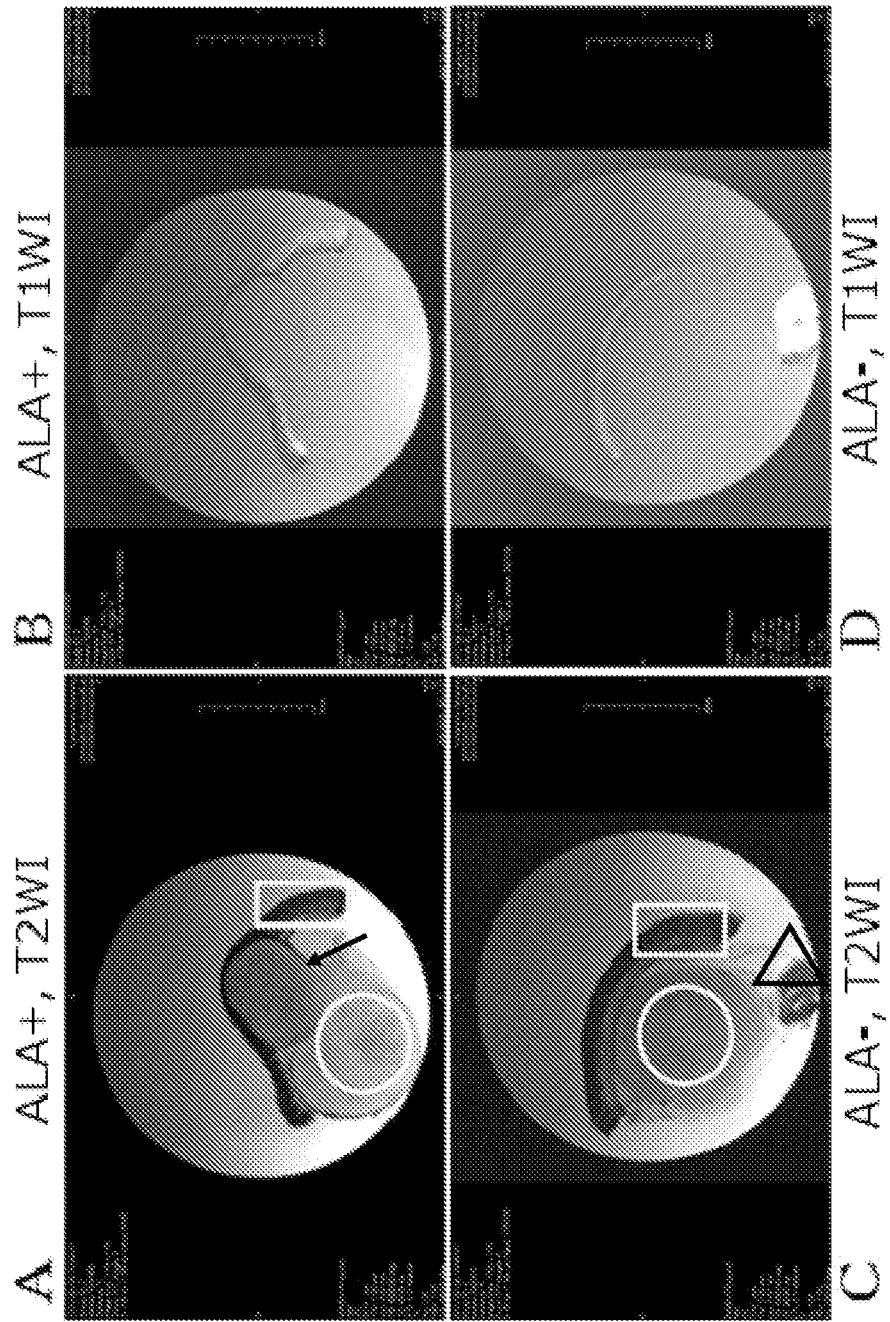
FIG. 2 is a view showing examples of a T1-weighted image and a T2-weighted image obtained by an MRI apparatus, with regard to an ALA administration group and a (negative) control group.
Figure 3:
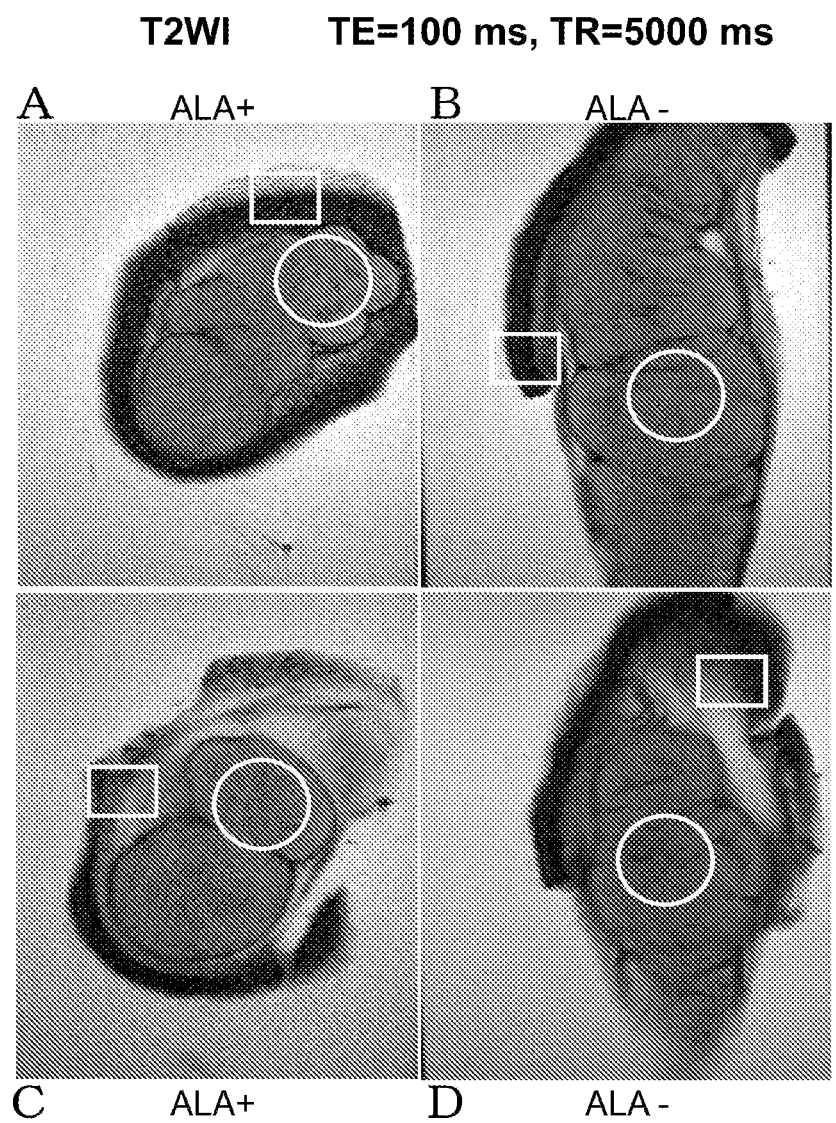
FIG. 3 is a view showing examples of T2-weighted images obtained by an MRI apparatus, with regard to an ALA administration group and a (negative) control group. The region enclosed by a white circle indicates a part of the section of a transplanted tumor portion. The region enclosed by a white square indicates a part of the section of non-tumor tissues (skin tissues, etc.) derived from a rat, into which tumor cells have been transplanted.

Some of the aforementioned images obtained by an MRI apparatus are shown in FIG. 2 and FIG. 3. These images were each obtained under the following conditions.

TABLE 2

|  | FIG. 2A (ALA+, T2WI) | FIG. 2B (ALA+, T1WI) | FIG. 2C (ALA−, T2WI) | FIG. 2D (ALA−, T1WI) | FIG. 3A and 3C (ALA+, T2WI) | FIG. 3B and 3D (ALA−, T2WI) |
| --- | --- | --- | --- | --- | --- | --- |
| FA(°) | 180 | 180 | 180 | 180 | 180 | 180 |
| TE (ms) | 99 | 11 | 99 | 11 | 100 | 100 |
| TR (ms) | 5000 | 5000 | 5000 | 5000 | 5000 | 5000 |
| NEX | 1 | 1 | 1 | 1 | 5 | 5 |
| Slice Thickness (mm) | 1 | 1 | 1 | 1 | 1 | 1 |
| Spacing between slices (mm) | 1.5 | 1.5 | 1.5 | 1.5 | 1.1 | 1.1 |
| Slices | 2 | 2 | 2 | 2 | 9 | 9 |
| Scan Plane | Axial | Axial | Axial | Axial | Axial | Axial |
| ETL | 2 | 2 | 2 | 2 | 6 | 6 |
| Pixel Bandwidth (Hz/Pix) | 262.6 | 262.6 | 262.6 | 262.6 | 267.1 | 267.1 |
| Acquisition Matrix (P × R) | 128 × 170 | 128 × 170 | 128 × 170 | 128 × 170 | 192 × 260 | 192 × 520 |
| Reconstruction Matrix | 170 × 170 | 170 × 170 | 170 × 170 | 170 × 170 | 260 × 260 | 260 × 260 |
| FOV (mm$^2$) | 27 × 27 | 27 × 27 | 27 × 27 | 27 × 27 | 26 × 26 | 26 × 26 |

When the region enclosed by a white circle (corresponding to a tumor portion section) in FIG. 2A (ALA administration group, T2-weighted image) was compared with the region enclosed by a white circle in FIG. 2C (control group, T2-weighted image), the region of the ALA administration group (FIG. 2A) was imaged in white (at high signals), compared to the control group (FIG. 2C). In other words, signals in the tumor region were enhanced (increased) in the T2-weighted image by administration of ALA.

It is to be noted that the region enclosed by a white square in each of FIG. 2A and FIG. 2C indicates a portion of the section of non-tumor tissues (skin tissues, etc.) derived from a rat, into which tumor cells have been transplanted.

The above described region enclosed by a white circle, which was imaged in (at high signals) in FIG. 2A (ALA administration group, T2-weighted image), corresponds to the set ROI, as described regarding FIG. 1. On the other hand, a circle portion, which was imaged in somewhat dark (at low signals) although it was a tumor portion section, was present near these regions. It is considered that such a difference in image contrasts was generated for the reason that since an imaging coil was present below the image and the circle portion was disposed in a portion in which sensitivity was reduced, signals were decreased and a change generated as a result of administration of ALA was hardly recognized. Otherwise, without wishing to be bound by any theory, it is also considered that such a difference in image contrasts would reflect a difference to such an extent that ALA was incorporated into tumor cells and was metabolically activated to PpIX or the like. For example, the black arrow in FIG. 2A indicates a circle portion, which was imaged in dark (at low signals) in the T2-weighted image although it was a tumor portion section, wherein the peripheral portion thereof was observed in a high signal zone. Such a change was not observed in the tumor portion section in the control group. Accordingly, it is considered that the region of the high signal zone in the ALA administration group, which is shown with the black arrow, suggests that tumor in the peripheral portion of the circle portion is sufficiently activated.

Also, when FIG. 3A and FIG. 3C (ALA administration group, T2-weighted image) were compared with FIG. 3B and FIG. 3D (control group, T2-weighted image), the section of the tumor portion (for example, the region enclosed by a white circle) in the ALA administration group (FIG. 3A and FIG. 3C) imaged in white (at high signals), compared to the control group (FIG. 3B and FIG. 3D).

INDUSTRIAL APPLICABILITY

The nuclear magnetic resonance diagnostic agent of the present invention can be advantageously used in the medical field.

What is claimed is:

1. A method for diagnosing glioblastoma in a subject, comprising:
   (1) a step of administering an MRI contrast agent comprising 5-aminolevulinic acid or a salt thereof orally to a living human or non-human animal subject,
   (2) a step of applying MRI to the living human or non-human animal subject, utilizing nuclear magnetic resonance, wherein the MRI employs the Rapid Acquisition with Relaxation Enhancement (RARE) method;
   (3) a step of obtaining a T2-weighted image of accumulated protoporphyrin IX with respect to the state of protons of the living human or non-human animal subject; and
   (4) a step of diagnosing a glioblastoma in the subject, based on the T2-weighted image with respect to the state of protons;
   wherein the T2 relaxation time in the presence of the MRI contrast agent has a value of 1.2 times or more of the value of the T2 relaxation time in the absence of the MRI contrast agent.

2. The method as recited in claim 1, wherein the step of diagnosing glioblastoma in the subject comprises the comparison of the T2-weighted image with a second T2-weighted image obtained in the absence of the MRI contrast agent.

3. The method according to claim 2, wherein the agent further comprises one or two or more metal-containing compounds.

4. The method according to claim 3, wherein the metal-containing compound is an iron-containing compound.

* * * * *